United States Patent
Mordaunt et al.

(10) Patent No.: US 9,427,358 B2
(45) Date of Patent: *Aug. 30, 2016

(54) PRESBYOPIC VISION CORRECTION WITH CONTROLLED 3-D PATTERNED MECHANICAL WEAKENING OF SCLERAL TISSUE

(71) Applicant: EOS HOLDINGS, LLC, Los Gatos, CA (US)

(72) Inventors: David H. Mordaunt, Los Gatos, CA (US); Robert E. Grant, Laguna Beach, CA (US)

(73) Assignee: EOS HOLDINGS, LLC, Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,721

(22) Filed: Sep. 14, 2015

(65) Prior Publication Data

US 2016/0000605 A1 Jan. 7, 2016

Related U.S. Application Data

(63) Continuation of application No. 13/136,365, filed on Jul. 29, 2011, now Pat. No. 9,161,857.

(60) Provisional application No. 61/400,617, filed on Jul. 29, 2010.

(51) Int. Cl.
*A61F 9/008* (2006.01)

(52) U.S. Cl.
CPC ......... *A61F 9/00838* (2013.01); *A61F 9/0084* (2013.01); *A61F 2009/00846* (2013.01); *A61F 2009/00865* (2013.01); *A61F 2009/00895* (2013.01)

(58) Field of Classification Search
CPC ............... A61F 9/008; A61F 9/00802; A61F 9/00804; A61F 9/004; A61F 9/00838; A61F 2009/00861; A61F 2009/00865
USPC ........................ 606/4–6; 607/88, 89; 128/898
See application file for complete search history.

(56) References Cited

U.S. PATENT DOCUMENTS

| | | | |
|---|---|---|---|
| 4,907,586 A | 3/1990 | Bille et al. | |
| 6,146,375 A | 11/2000 | Juhasz et al. | |
| 6,745,775 B2 | 6/2004 | Lin | |
| 6,824,540 B1 | 11/2004 | Lin | |
| 7,655,002 B2 | 2/2010 | Myers | |
| 9,161,857 B2 * | 10/2015 | Mordaunt | A61F 9/00838 |
| 2006/0111775 A1 | 5/2006 | Schachar | |
| 2006/0253111 A1 * | 11/2006 | Van Valen | A61F 9/008 606/5 |
| 2008/0065055 A1 | 3/2008 | Jones | |
| 2008/0097418 A1 | 4/2008 | Jones | |
| 2010/0076417 A1 | 3/2010 | Suckewer | |
| 2012/0029489 A1 | 2/2012 | Mordaunt et al. | |

* cited by examiner

*Primary Examiner* — Ahmed Farah
(74) *Attorney, Agent, or Firm* — Innovation Counsel LLP

(57) ABSTRACT

Treatments to improve ocular conditions such as presbyopia are provided. Structural (mechanical) weakening of the sclera is accomplished through the formation of a 3-D pattern of laser foci in the sclera resulting in an increase in the range of ocular accommodation.

9 Claims, 7 Drawing Sheets

PRESBYOPIC VISION CORRECTION WITH CONTROLLED 3-D PATTERNED MECHANICAL WEAKENING OF SCLERAL TISSUE

CROSS REFERENCE TO RELATED APPLICATIONS

This application is a continuation of U.S. patent application Ser. No. 13/136,365 filed Jul. 29, 2011, which claims priority from U.S. Provisional Patent Application 61/400,617 filed Jul. 29, 1010, both of which are incorporated herein by reference in their entirety.

FIELD OF THE INVENTION

The invention relates to presbyopic vision correction devices and methods.

BACKGROUND

Presbyopia is a health condition where the eye exhibits a progressively diminished ability to focus on near field objects with age. Presbyopia's exact mechanisms are not known with certainty. The research evidence supports a loss of elasticity of the crystalline lens. In addition changes in the curvature of the lens from continual growth and loss of power of the ciliary muscles (the muscles that bend and straighten the lens) have also been postulated as its cause.

Standard of care of presbyopia is the use of reading glasses. Other approaches have been utilized including accommodative intra-ocular lenses (IOLs), multifocal IOLs, multifocal Lasik and other approaches involving optical correction.

US 2010/0076417 discussed the concept of removing or altering the crystalline lens with ultrashort laser pulses. Others (e.g. U.S. Pat. No. 6,824,540, U.S. Pat. No. 6,745,775, US 2006/0253111, US 2008/0065055 and US 2008/0097418) discussed the concept of removing scleral tissue to treat presbyopia. The treatment of presbyopia taught in these references pertains to making channels in the sclera by tissue ablation on the order of magnitude of 400-700 microns and specifically through over 60% of the scleral thickness.

Some of the main issues with these scleral treatment approaches, for example, are cosmetic discoloration of the sclera after treatments, lack of customization of the procedures to the patient's degree of accommodation or response to treatment, and the fact that these are invasive procedures done in the operating room environment.

Accordingly there is a need in the art to overcome at least some of the issues and develop new techniques for the treatment of presbyopia.

SUMMARY

The invention provides a method and system to improve ocular conditions such as presbyopia by increasing the range of ocular accommodation. Structural (mechanical) weakening of the sclera is accomplished through the formation of a 3-D (layered) pattern of laser foci in the sclera without causing ablation of areas of the conjunctiva. In fact, the focused laser pulses are noninvasive to the conjunctiva. As a result of the placement of this 3-D pattern of laser foci, the sclera could become more elongated or could have increased elasticity therewith improving the range of ocular accommodation from distance to intermediate and near vision, i.e., lessening the effects of presbyopia.

DETAILED DESCRIPTION

The present invention pertains to a method and system of structurally weakening tissue to improve a medical condition. A key objective of the invention is to use a laser system to direct a three-dimensional (3-D) pattern of focused laser pulses noninvasively through a first tissue layer while causing a 3-D (layered) pattern of laser foci in a second tissue layer underneath the first tissue layer (FIGS. 1-5). In one example, structural weakening is caused in the sclera (second tissue layer) when treating presbyopia. The 3-D pattern of laser pulses is directed noninvasively through the conjunctiva (first tissue layer) and focused at the sclera tissue. Structurally weakening is defined as changing the mechanical properties at or near the laser focus in the second tissue layer. For example, the sclera tissue could be elongated or could have increased elasticity due to these laser foci. Noninvasive tissue interaction is achieved, by keeping the tissue intact in the first tissue layer, and only affecting tissue in the second tissue layer in the regions near or at the laser foci.

In one example, each of the generated laser foci affect a tissue region which can be defined by a 3-D ellipsoidal shape. In a specific example, each of the 3-D ellipsoidal shapes has a minor axis of 6 micrometers to 50 micrometers and a major axis of 50 micrometers to 300 micrometers.

To ensure therapeutic levels of treatment the focused laser beam pulses could have a pulse-width of 1 femtosecond to 500 picoseconds combined with a suitable peak power to ensure structural weakening. In another embodiment, each of the focused laser pulses could have a pulse-width of 1 femtosecond to 500 picoseconds and a peak power in a range of 10 kW to 24 kW or a range of 10 kW to 60 kW. In yet another embodiment, each of the focused laser pulses has a pulse-width of 1 femtosecond to 10 nanoseconds and a suitable peak power to ensure structural weakening. Still in another embodiment, each of the focused laser pulses has a pulse-width of 1 femtosecond to 10 nanoseconds and a peak power in a range of 10 kW to 24 kW or a range of 10 kW to 60 kW.

Figure 1:
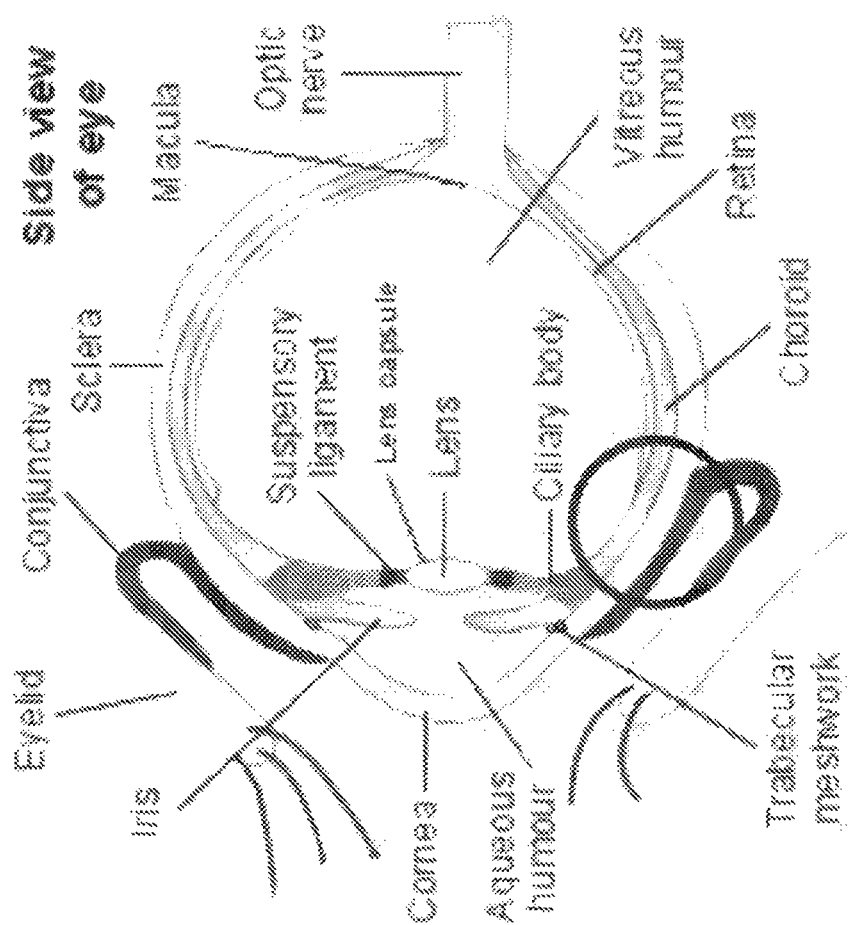
FIG. 1 shows a cross-section of an eye with the circled area representing a region of treatment according to an exemplary embodiment of the invention.
Figure 2:
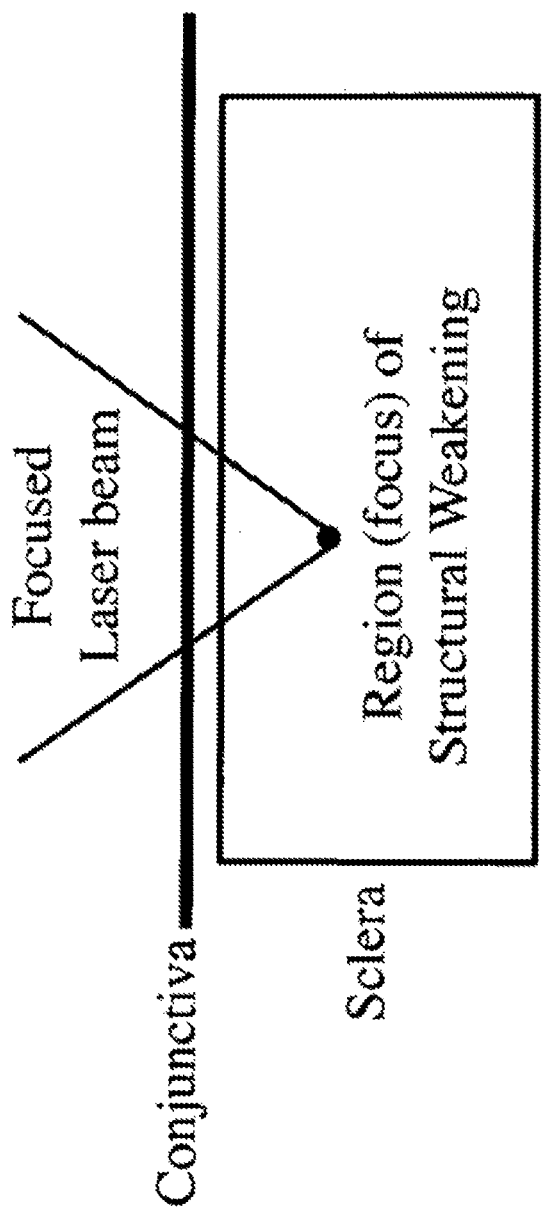
FIG. 2 shows an example of the focused laser beam interaction with the tissue according to an exemplary embodiment of the invention. The focus is the focal point of the laser beam.
Figure 3:
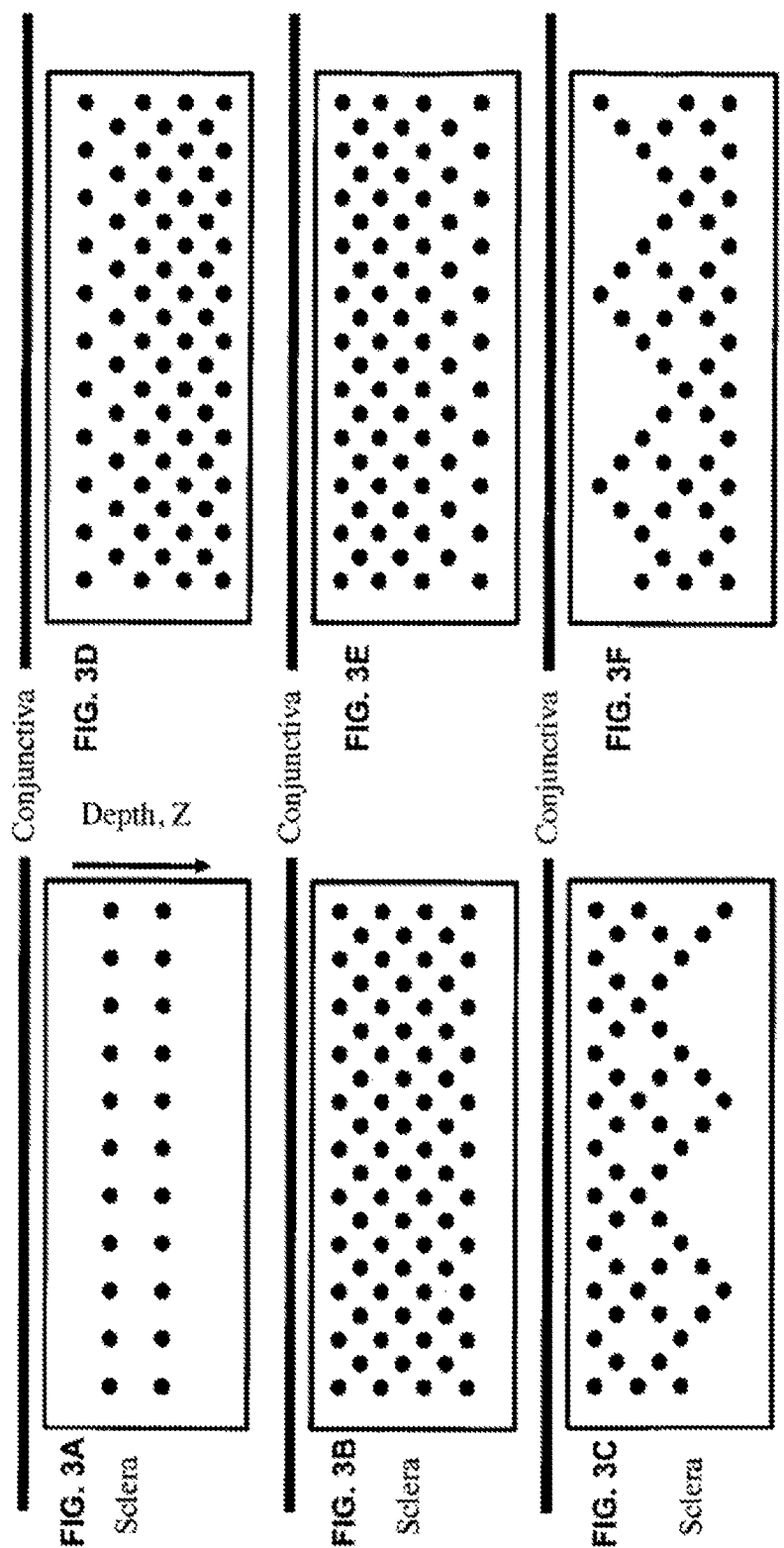
FIGS. 3A-3F show each according to an exemplary embodiment of the invention cross-sections through the conjunctiva and sclera with the dots in the sclera representing examples of the 3-D pattern of laser foci, which are structurally/mechanically weakened regions.
Figure 4:
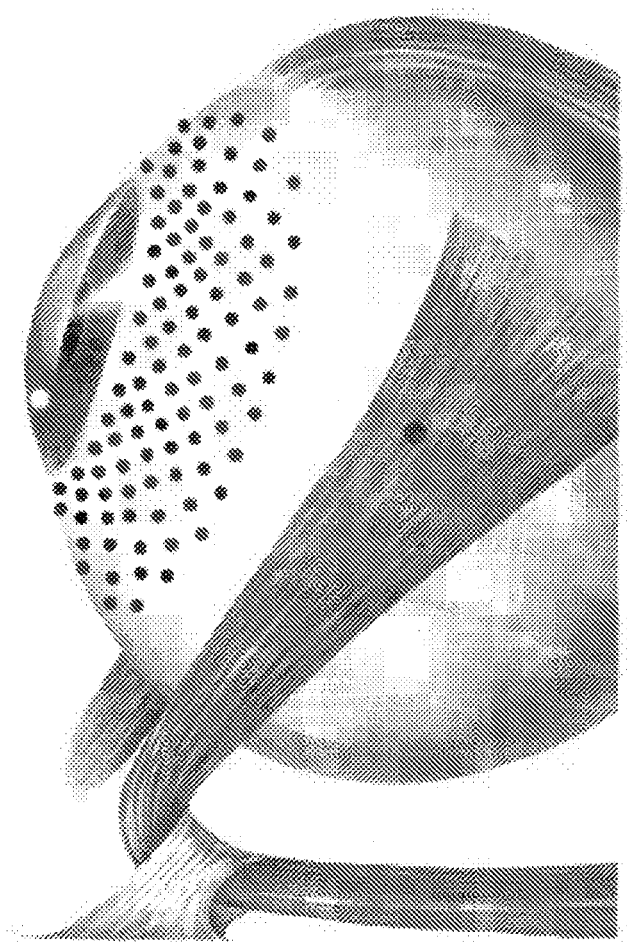
FIG. 4 shows an example of the surface positioning of the targeted tissue, with the understanding of the depth modulation as shown in FIGS. 3A-3F according to an exemplary embodiment of the invention.
Figure 5:
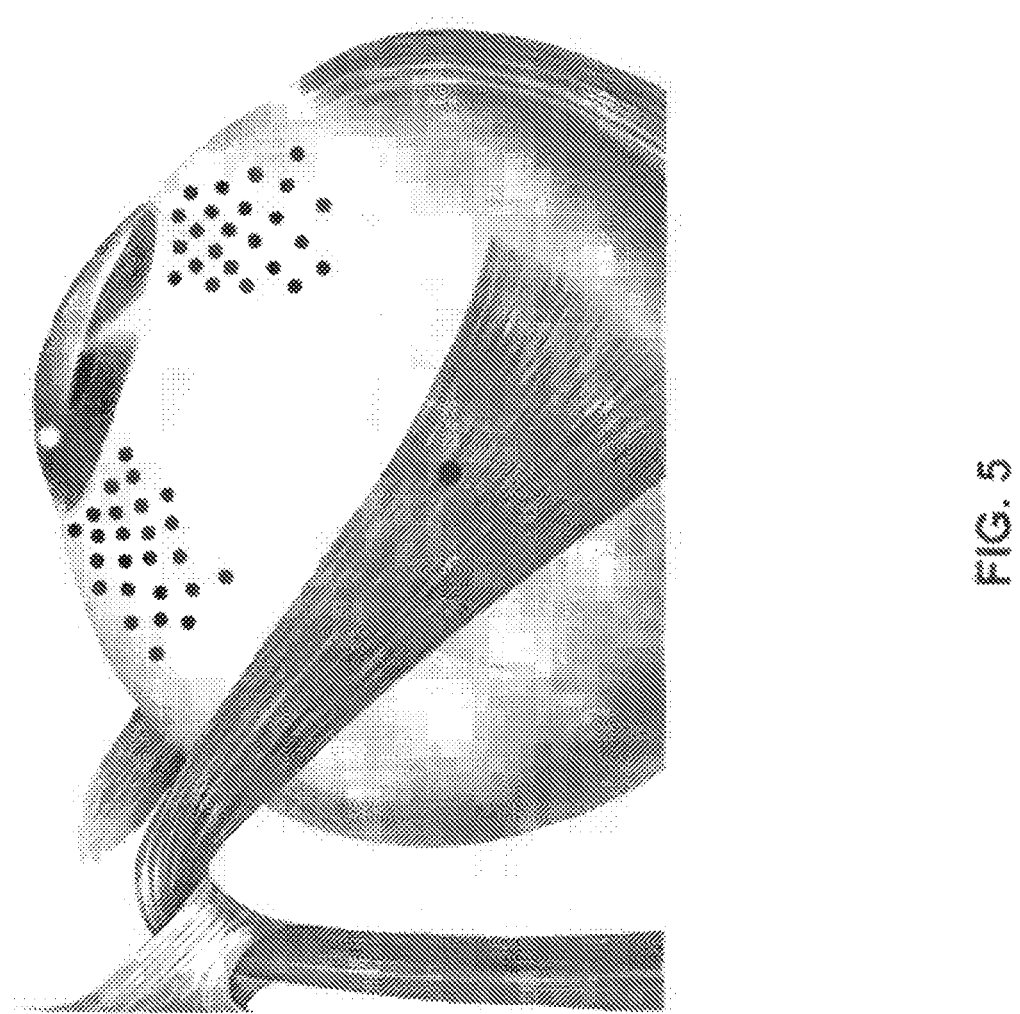
FIG. 5 shows an example of a treatment of the quadrants avoiding the rectus muscles with the understanding of the depth modulation as shown in FIGS. 3A-3F according to an exemplary embodiment of the invention.
Figure 6:
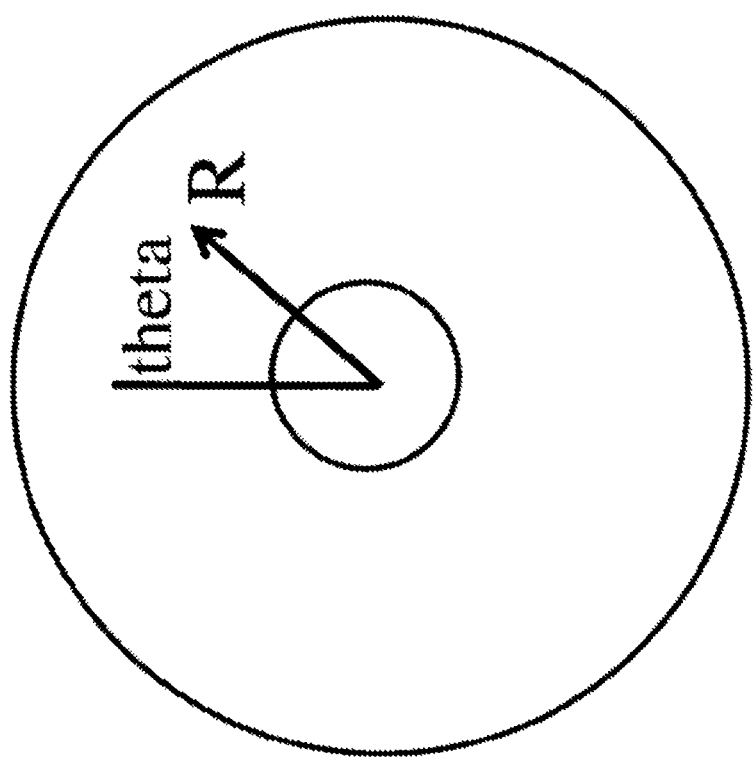
FIG. 6 shows an example of scanning patterns in polar coordinates and depth according to an exemplary embodiment of the invention.

In operation, a pulsed laser could be used to scan in 3-D over at least a portion of the orbit of an eye (FIGS. 4-5). The scanning coordinate system could be defined in X, Y and Z coordinates or in polar coordinates (R, theta) as shown in FIG. 6. The scan could also be expressed in terms of R, theta and Z. The 3-D patterns may cover 360 degrees or could be in quadrants avoiding the rectus muscles and their attachments (FIGS. 4-5).

In one embodiment, an eye tracking system may be included to allow for safe delivery of the focused laser pulses to the tissue. In another embodiment, a real-time monitoring and feedback system could be included to monitor the optical characteristics of the eye to determine the extent of treatment. Examples of optical characteristics are geometry of the eye, distances within the eye (thickness of the lens, cornea to anterior capsule and/or parts of the lens along the optical axis). Optical characteristics could further include direct or indirect measurements of ocular accommodation.

Figure 7:
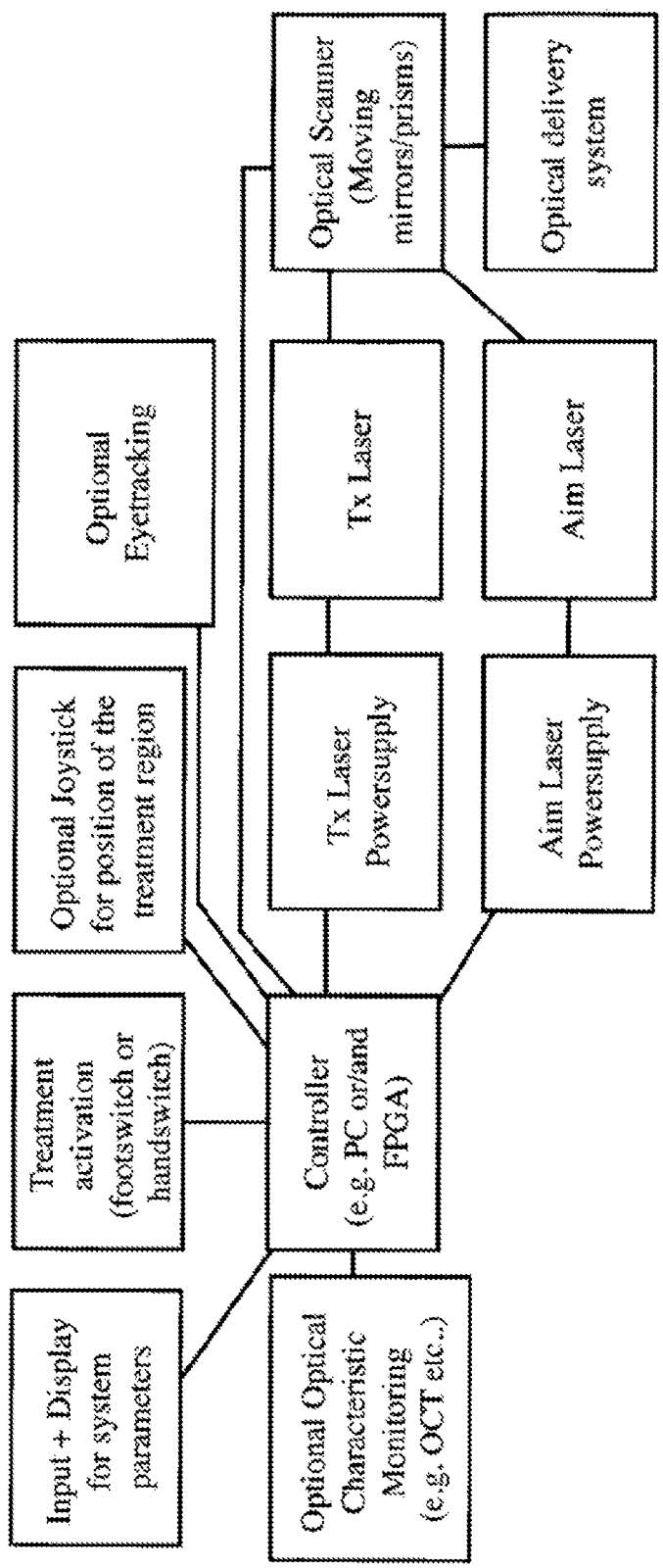
FIG. 7 shows an example of a system according to an exemplary embodiment of the invention.

The extent of the treatment is determined by the number of laser treatment foci, the number of layers (in depth) and the size of the region defined in (X, Y and Z, or R and theta). In addition, the degree of preoperative accommodation may determine the extent of treatment. Furthermore, real-time monitoring on a shot-by-shot basis may determine the extent of treatment during a session. During a session, treatment parameters can be adjusted such as a transition from standby to ready, aim beam intensity, treatment energy, power or fluence, pattern selection including selection of size of region to be treated. FIG. 7 shows an example of device elements for implementation of embodiments of the invention, which could be combined in any combination or form as long as it meets the key objective of the invention as described herein.

What is claimed is:

1. A method of structurally weakening the sclera in an eye to improve a presbyopia condition of the eye, the method comprising:

using a pulsed laser system to generate a three-dimensional (3-D) pattern of focused laser pulses in the sclera, the laser pulses passing noninvasively through a conjunctiva layer in the eye to a plurality of foci in the sclera to structurally weaken the sclera at the foci, thereby producing a 3-D pattern of structurally weakened regions in the sclera that increases the eye's range of ocular accommodation and improves the presbyopia condition;

wherein each of the structurally weakened regions in the sclera has a 3-D ellipsoidal shape.

2. The method as set forth in claim 1, wherein the 3-D pattern of structurally weakened regions in the sclera elongates the sclera.

3. The method as set forth in claim 1, wherein the 3-D pattern of structurally weakened regions in the sclera increases the elasticity of the sclera.

4. The method as set forth in claim 1, wherein each of the 3-D ellipsoidal shapes has a minor axis of 6 micrometers to 50 micrometers and a major axis of 50 micrometers to 300 micrometers.

5. The method as set forth in claim 1, wherein each of the focused laser pulses has a pulse-width of 1 femtosecond to 500 picoseconds and a suitable peak power to ensure structural weakening of the sclera.

6. The method as set forth in claim 1, wherein each of the focused laser pulses has a pulse-width of 1 femtosecond to 500 picoseconds and a peak power in a range of 10 kW to 60 kW.

7. The method as set forth in claim 1, wherein each of the focused laser pulses has a pulse-width of 1 femtosecond to 10 nanoseconds and a suitable peak power to ensure structural weakening of the sclera.

8. The method as set forth in claim 1, wherein each of the focused laser pulses has a pulse-width of 1 femtosecond to 10 nanoseconds and a peak power in a range of 10 kW to 60 kW.

9. The method as set forth in claim 8, wherein each of the focused laser pulses has a peak power in the range of 10 kW to 24 kW.

* * * * *